(12) United States Patent
Sicken et al.

(10) Patent No.: US 6,569,974 B1
(45) Date of Patent: May 27, 2003

(54) POLYMERIC PHOSPHINIC ACIDS AND SALTS THEREOF

(75) Inventors: Martin Sicken, Köln (DE); Norbert Weferling, Hürth (DE); Hans-Peter Schmitz, Brühl (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/532,193

(22) Filed: Mar. 22, 2000

(30) Foreign Application Priority Data

Mar. 22, 1999 (DE) ......................................... 199 12 920

(51) Int. Cl.7 ............................................... C08F 30/02
(52) U.S. Cl. ...................................... 526/274; 526/275
(58) Field of Search ................................ 526/274, 275

(56) References Cited

U.S. PATENT DOCUMENTS

| | | | |
|---|---|---|---|
| 3,734,954 A | * | 5/1973 | Maier .................... 260/502.4 P |
| 5,811,575 A | | 9/1998 | Kleiner et al. |
| 6,090,968 A | | 7/2000 | Hörold et al. |
| 6,232,493 B1 | | 5/2001 | Weferling et al. |
| 6,242,642 B1 | | 6/2001 | Weferling et al. |
| 6,278,012 B1 | | 8/2001 | Hörold et al. |
| 6,300,516 B1 | | 10/2001 | Weferling et al. |
| 6,329,544 B1 | | 12/2001 | Weferling et al. |
| 6,355,832 B1 | | 3/2002 | Weferling et al. |
| 6,359,171 B1 | | 3/2002 | Weferling et al. |

FOREIGN PATENT DOCUMENTS

| DE | 1 943 577 | 5/1970 |
|---|---|---|
| DE | 198 51 618 | 6/1999 |

OTHER PUBLICATIONS

Houben–Weyl, Supplementary vol. 20, "Polymerisation durch radikalische Initiierung", p. 15–74, 1987.
U.S. patent application Ser. No. 08/466,493, filed Jun. 6, 1995, Bansi, et al.
U.S. patent application Ser. No. 09/198,540, filed Nov. 24, 1998, Weferling, et al.
U.S. patent application Ser. No. 09/469,104, filed Dec. 21, 1999, Weferling, et al.
U.S. patent application Ser. No. 09/742,822, filed Dec. 21, 2000, Dookhith, et al.
U.S. patent application Ser. No. 10/025,739, filed Dec. 19, 2001, Sicken, et al.
Chemical Abstracts XP–002138314, vol. 101, No. 11, Sep. 10, 1984, Columbus, Ohio, US; abstract No. 91509, Reaction of Acetylenes with Acid Hydrophosphoryl Compounds.
Kosolapoff, G. M., Organic Phosphorus Compounds, vol. 6, Wiley–Interscience, 1973.
Mastalerz, Przemyslaw, Synthesis Of Some Ethylene–(P, P'–Dialkyl)–Diphosphinic Acids As New Potential Antimetabolites Of Succinic Acid, Poczniki Chem 38, 61, 1964.
Block B.P., Polymeric Metal Phosphinates, Inorganic Macromol Reviews, 1, 1970, pp. 115–125.
Nifant'ev, É. E., Reactions Of Acetylenes With Hypophosphorous and Phosphorous Acids, Shurnal Obshchei Khimii, 56, 4, pp. 773–781.

* cited by examiner

*Primary Examiner*—David W. Wu
*Assistant Examiner*—William K. Cheung
(74) *Attorney, Agent, or Firm*—Anthony A. Bisulca

(57) ABSTRACT

The invention relates to polymeric phosphinic acids and their salts of the formula (I)

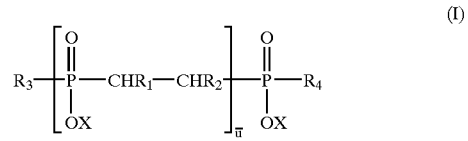

in which

X is hydrogen or a 1/m metal of valency m, $R_1$ and $R_2$ are identical or different and are hydrogen, a carboxyl group, a carboxylic acid derivative, an unsubstituted or substituted alkyl group having 1 to 10 carbon atoms, phenyl, benzyl or alkyl-substituted aromatics, $R_3$ and $R_4$ are identical or different and are hydrogen or a vinyl group of the formula (VI)

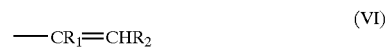

in which $R_1$ and $R_2$ have the abovementioned meaning, and ū is the average number of monomer units. The invention also relates to a process for the preparation of the abovementioned compounds and their use.

21 Claims, No Drawings

POLYMERIC PHOSPHINIC ACIDS AND SALTS THEREOF

BACKGROUND OF THE INVENTION

The present invention relates to novel polymeric phosphinic acids and their salts, to a process for their preparation, and to their use.

DESCRIPTION OF THE RELATED ART

Phosphinic acids and their salts can be prepared by a variety of methods and have been widely described. For example, a comprehensive overview is Bound in Kosolapoff, Maier: *"Organic Phosphorus Compounds"*, Volume 6. Wiley-Interscience, 1973. The compounds known hitherto are mostly monomeric phosphinic acids, i.e. Phosphinic acids which contain only one phosphinic acid group. Come diphosphinic acids and their salts are also Known, for example ethane-1,2-diethylphosphinic acid (P. Mastalerz, Roczniki Chem. 38, 61 (1964).

Mention of polymeric phosphinic acids have so far been limited to coordination polymers in which monomeric phosphinic acids function as bridge ligands for metal ions. An overview of this group of products, known as polymeric metal phosphinates, is found in: B. P. Block, *Inorg. Macromol. Rev.*, 1 (1970) 115–125.

The free-radical-initiated reaction of olefins with hypophosphorous acid is known and, as described in the as yet unpublished German patent application (file reference P19851618.5-44), gives the corresponding monomeric phosphinic acids.

The free-radical-initiated reaction of acetylenes with hypophosphorous acid has also been studied [Nifant'ev et al., Zh. Obshch. Khim. (1986), 56(4) p. 773–781]; the reaction products obtained were merely mixtures of vinylphosphonous acids, divinylphosphinic acids and diphosphonous acids.

SUMMARY OF THE INVENTION

"Genuine" polymeric phosphinic acids, i.e. polymeric phosphinic acids with a structure based on covalent bonding and with phosphinic acid groupings in the repeat units, were not previously known.

DESCRIPTION OF THE PREFERRED EMBODIMENTS

The invention therefore provides polymeric phosphinic acids and their salts of the formula (I)

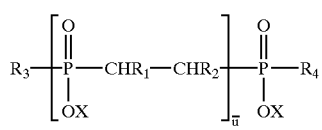

in which

X is hydrogen or a 1/m metal of valency m, $R_1$ and $R_2$ are identical or different and are hydrogen, a carboxyl group, a carboxylic acid derivative, an unsubstituted or substituted alkyl group having 1 to 10 carbon atoms, phenyl, benzyl or alkylsubstituted aromatics, $R_3$ and $R_4$ are identical or different and are hydrogen or a vinyl group of the formula (VI)

$$—CR_1=CHR_2 \quad (VI)$$

in which $R_1$ and $R_2$ have the abovementioned meaning, and $\bar{u}$ is the average number of monomer units.

X is preferably a metal of groups IA, IIA, IIIA, IVA, VA, IIB, IVB, VIIB, VIIIB of the Periodic Table or is cerium.

The metal is preferably Li, Na, K, Mg, Ca, Sr, Ba, Al, Ge, Sn, Sb, Bi, Zn, Ti, Zr, Mn, Fe and/or Ce.

The metal is particularly preferably Na, Ca, Al and/or Zn.

X is preferably H.

Preferably, $R_1$ and $R_2$ are identical or different and are hydrogen or an unsubstituted or substituted alkyl group having 1 to 10 carbon atoms.

Preferably, $R_1$ and R2 are identical or different are and hydrogen or an unsubstituted or substituted alkyl group having 1 to 10 carbon atoms, where the substituents are one or more of the groups OH, CN or $NH_2$.

Preferably, $R_1$ and $R_2$ are identical or different and are hydrogen or an alkyl group having from 1 to 4 carbon atoms and substitution by one or two OH groups.

Preferably, $R_1$ and $R_2$ are identical or different and are hydrogen or a carboxylic acid derivative.

Preferably, $R_1$ and $R_2$ are identical or different and are hydrogen or a carboxylic acid derivative of the formula COOR, where R is an alkyl group having from 1 to 4 carbon atoms.

$R_3$ and $R_4$ are preferably hydrogen.

Each of $R_3$ and $R_4$ is preferably a vinyl group of the formula $—CR_1=CHR_2$ (VI), in which $R_1$ and $R_2$ have the abovementioned meanings.

$R_3$ is preferably H and $R_4$ is preferably a vinyl group of the formula $—CR_1=CHR_2$ (VI), in which $R_1$ and R2 have the abovementioned meanings.

$R_3$ is preferably a vinyl group of the formula $—CR_1=CHR_2$ (VI), in which $R_1$ and $R_2$ have the abovementioned meanings and $R_4$ is H.

Each of $R_1$ and R2 is preferably an identical or different alkyl group having 1 to 10 carbon atoms or is hydrogen, if at least one of the groups $R_3$ or $R_4$ is a vinyl group of the formula $—CR_1=CHR_2$.

The present invention in particular provides polymeric phosphinic acids and their salts of the formulae

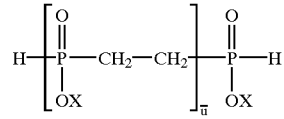

where X=H or 1/m metal

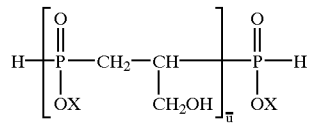

where X=H or 1/m metal $$\left[ H - \underset{\underset{OX}{|}}{\overset{\overset{O}{\|}}{P}} - \underset{\underset{CH_2OH}{|}}{CH} - \underset{\underset{CH_2OH}{|}}{CH} - \underset{\underset{OX}{|}}{\overset{\overset{O}{\|}}{P}} - H \right]_{\overline{n}}$$

where X=H or 1/m metal $$\left[ H - \underset{\underset{OX}{|}}{\overset{\overset{O}{\|}}{P}} - \underset{\underset{COOR}{|}}{CH} - \underset{\underset{COOR}{|}}{CH} - \underset{\underset{OX}{|}}{\overset{\overset{O}{\|}}{P}} - H \right]_{\overline{n}}$$

where X=H or 1/m metal

The invention also provides a process for preparing polymeric phosphinic acids and their salts of the formula (I) which comprises reacting hypophosphorous acid and/or its alkali metal salts with acetylenes of the formula (II)

$$R_1 - C \equiv C - R_2 \quad (II)$$

in which $R_1$ and $R_2$ are identical or different and are hydrogen, a carboxyl group, a carboxylic acid derivative, an unsubstituted or substituted alkyl group having 1 to 10 carbon atoms, phenyl, benzyl or alkylsubstituted aromatics.

Preference is given to reacting alkali metal salts of hypophosphorous acid with acetylenes of the formula (II) and then reacting the resultant alkali metal salts of the polymeric phosphinic acid with at least one metal compound of groups IA, IIA, IIIA, IVA, VA, IIB, IVB, VIIB, VIIIB of the Periodic Table, or with a cerium compound. This process therefore includes the conversion of a first alkali metal salt of the polymeric phosphinic acid into another alkali metal salt of the polymeric phosphinic acid.

Preference is given to reacting the hypophosphorous acid with acetylenes of the formula (II) and then reacting the resultant polymeric phosphinic acids with at least one metal compound of groups IA, IIA, IIIA, IVA, VA, IIB, IVB, VIIB, VIIIB of the Periodic Table, or with a cerium compound.

The metal compound is preferably a compound of Li, K, Na, Mg, Ca, Sr, Ba, Al, Ge, Sn, Sb, Bi, Zn, Ti, Zr, Mn, Fe and/or Ce.

Preference is given to reacting alkali metal salts of hypophosphorous acid with acetylenes of the formula (II) and then reacting the resultant alkali metal salts of the polymeric phosphinic acid with an acid to give the polymeric phosphinic acid. The resultant polymeric phosphinic acid may then be subjected to one or more of the above-mentioned process steps.

There are therefore various ways of modifying the variable X in formula (I) as formulated above. If, for example, a starting material used for the reaction described above with acetylenes is readily obtainable alkali metal salts of hypophosphorous acid, the corresponding polymeric alkali metal phosphinates are produced, for example where X=Li, Na or K in formula (I). If hypophosphorous acid is used as a starting material, the free polyphosphinic acids are produced, where X=H in formula (I). The latter may also be obtained by acidifying the alkali metal phosphinates.

Using common precipitation and salt interchange reactions and starting from the alkali metal salts of the polyphosphinic acids or from the free polyphosphinic acids, it is possible to obtain polyphosphinic acid salts of a wide variety of metals, for example those of the alkaline earth metals, of the metals in main groups II to V, and also of transition group metals.

It is preferable to, use from 0.6 to 1.5 mol, of acetylene of the formula (II) per mole of hypophosphorous acid or of its alkali metal salt.

It is preferable to carry out the reaction in the presence of a free-radical initiator.

An overview of compounds of this type and their mode of operation is found, for example, in: Houben-Weyl, Supplementary Volume 20, Section entitled *"Polymerisation durch radikalische Initiierung"* [Free-radical-initiated polymerization], pp. 15–74.

Preference is given to the use of azo compounds as free-radical-initiators.

The azo compounds used are preferably cationic and/or noncationic azo compounds.

The cationic azo compounds used are preferably comprise 2,2'-azobis(2-amidinopropane) dihydrochloride or 2,2'-azobis(N,N'-dimethyleneisobutyramidine) dihydrochloride.

The noncationic azo compounds used are preferably azobis(isobutyronitrile), 4,4'-azobis(4-cyanopentanoic acid) or 2,2'-azobis(2-methylbutyronitrile).

The free-radical initiators used are preferably inorganic peroxidic and/or organic peroxidic. free-radical initiators.

The inorganic peroxidic free-radical initiators used are preferably hydrogen peroxide, ammonium peroxodisulfate and/or potassium peroxodisulfate.

The organic peroxidic free-radical initiators used are preferably dibenzoyl peroxide, di-tert-butyl peroxide and/or peracetic acid.

The reaction preferably takes place in a polar solvent.

The polar solvent is preferably acetic acid.

The reaction preferably takes place at a temperature of from 20 to 180° C.

The reaction particularly preferably takes place at a temperature of from 80 to 120° C.

The reaction preferably takes place in a pressure reactor. This applies in particular if the boiling point of the, acetylenes is below the reaction temperature.

In another preferred embodiment of the invention, the process is carried out at atmospheric pressure.

The starting material preferably used is hypophosphorous acid and/or alkali metal salts of hyophosphorous acid.

The use of sodium hypophosphite is particularly preferred.

The acetylenes used may be either unsubstituted acetylene itself, where $R_1$ and $R_2$=H in formula (II), singly substituted derivatives, where $R_1$=H and $R_2 \neq H$ in formula (II), or else disubstituted acetylenes, where $R_1$ and $R_2 \neq H$ in formula (II).

Examples of suitable acetylenes are the alkynes ethyne, phenylacetylene, diphenylacetylene, propyne, 1-butyne, 2-butyne, 1-phenylbutyne, 1-pentyne, 2-pentyne, 1-phenyl-1-pentyne, 1-hexyne, 2-hexyne, 3-hexyne, 1-phenyl-1-hexyne, 1-heptyne, 1-octyne, 4-octyne, 1-nonyne, 1-decyne and 1-dodecyne, the alkynols propargyl alcohol, 1-butyn-3-ol, 2-butyn-1-ol, 2-butyne-1,4-diol, 1-pentyn-3-ol, 2-pentyn-1-ol, 4-pentyn-1-ol, 4-pentyn-2-ol, 3-hexyn-1-ol, 5-hexyn-1-ol, 3-hexyne-2,5-diol, 2-octyn-1-ol, 1-octyn-3-ol, 3-nonyn-1-ol, 3-decyn-1-ol, and also propargyl chloride, propargyl bromide, propargylamine, propiolic acid, methyl propiolate, ethyl propiolate, 2-butynoic acid, ethyl 2-butynoate, 4-pentynoic acid, 5-hexynonitrile, 2-octynoate, methyl 2-octynoate, methyl 2-nonynoate, acetylenedicarboxylic acid, diethyl acetylenedicarboxylate and dimethyl acetylenedicarboxylate.

Preferred acetylenes are the 1-alkynes, propargyl alcohol, butynediol, propiolic acid and derivatives of acetylenedicarboxylic acid.

Particular preference is given to the use of ethyne (acetylene) itself.

Finally, the invention also provides the use, as flame retardants, of the novel polymeric phosphinic acids and of their salts.

The polymeric phosphinic acids and their salts are preferably used as flame retardants in thermoplastic polymers.

They may also be used for preparing synthetic building blocks for synthesis in organophosphorus chemistry.

The novel polymeric phosphinic acids and their salts may be described by the formula (I)

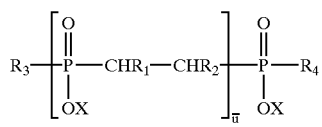

in which X is hydrogen or a 1/m metal of valency m, $R_1$ and $R_2$ are identical or different and are hydrogen, a carboxyl group, a carboxylic acid derivative, an unsubstituted or substituted alkyl group having 1 to 10 carbon atoms, phenyl, benzyl or alkyl-substituted aromatics, $R_3$ and $R_4$ are identical or different and are hydrogen or a vinyl group of the formula (VI)

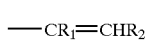

in which $R_1$ and $R_2$ have the abovementioned meaning, and $\overline{u}$ is the average number of monomer units. $\overline{u}$ is preferably from 2 to 1000, but if desired may also assume higher values.

As is usual in polymer terminology, $\overline{u}$ is the average number of monomer units and is calculated from the total number of monomer units per polymer molecule and the distribution (frequency) of each type of polymer molecule.

As defined below and using the reaction scheme A given further below, u, which like $\overline{u}$ gives the relative number of monomer units, may be any desired number from 0 to 10,000, or if desired above 10,000, in the (simplified) formula (Ia)

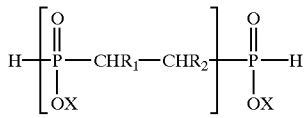

If the value for u is 1 (and X is hydrogen) in the abovementioned (simplified) formula (Ia) we have ethylenediphosphonous acid as in formula (V). Dimers, trimers, etc. can be obtained similarly.

For polymeric phosphinic acids and their salts where the value is relatively small (e.g. $\overline{u}$=3), this average chain length $\overline{u}$ represents values of u which are predominantly within the range from 0 to about 6, while the frequency of medium and relatively long polymer chains declines toward zero.

Conversely, if the value of $\overline{u}$ is very high (e.g. $\overline{u}$=500), the number of monomers, dimers, trimers, etc. is insignificant or zero and u, i.e. the relative number of monomer units, tends toward larger numeric values, in particular here within the range from 350 to 700.

Surprisingly, it has now been found that a broad range of the abovementioned polymeric phosphinic acids and their salts can be prepared in a simple and particularly cost-effective manner, in particular by free-radical-initiated polyaddition of acetylenes to hypophosphorous acid and, respectively, to salts thereof.

The claimed polymeric phosphinic acids and their salts are prepared by reacting hypophosphorous acid and, respectively, its (alkali metal) salts, preferably in the presence of a free-radical initiator, with acetylenes of the general formula (II)

where $R_1$ and $R_2$ in the formula above may be identical or different and are hydrogen, a carboxyl group, a carboxylic acid derivative, an unsubstituted or substituted alkyl group having 1 to 10 carbon atoms, phenyl, benzyl or alkyl-substituted aromatics.

Depending on the reactivity of the materials used, the products are polyphosphinic acids having phosphonous acid end groups (type A, reaction scheme A) or polyphosphinic acids having vinyl end groups (type B in reaction scheme B on page 12).

The basic principle of the polyaddition which leads to type A can be described, for example, by the following simplified reaction scheme A for the example of the reaction of free hypophosphorous acid:

Reaction scheme A:

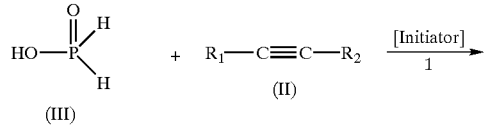

Hypophosphorous acid

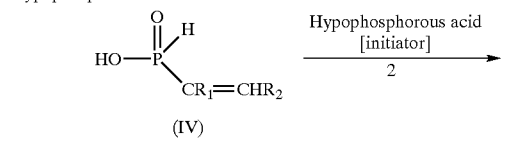

Vinylphosphonous acid

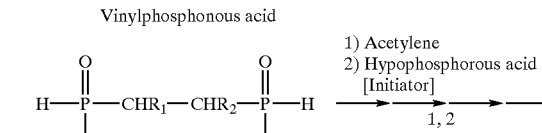

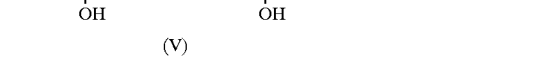

Ethylenediphosphonous acid

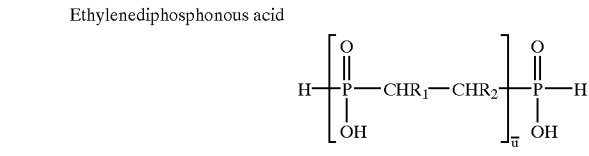

Polyethylene phosphinic acid

In a first stage (1) which uses a free-radical initiator, there is an addition reaction involving a P-H bond of the hypophosphorous acid and the triple bond of the acetylene. This gives a vinylphosphonous acid (IV), and in a second stage (2) under the same reaction conditions the double bond of this is involved in an addition reaction with another hypophosphite molecule. The resultant diphosphonous acid (V)

undergoes an addition reaction in a manner described above with further acetylene units and hypophosphite units, to give polyphosphinic acids (I).

$^{31}$P NMR spectroscopy can be used during the reaction to follow the build-up of the chain. The integral for the phosphonous acids signal group at δ=about 30 ppm ($Int_{phosphonous\ acids}$) here represents the end groups which are present, while the integral for the phosphinic acids signal group at δ=about 55 ppm ($Int_{phosphinic\ acids}$) gives the number of nonterminal groups. The chain length is calculated from the following formula:

$$\bar{u} = 1 + \frac{2 \cdot Int_{phosphinic\ acids}}{Int_{phosphonous\ acids}}$$

This formula can also be used to determine the final chain length of the polymeric phosphinic acids and thus also the average molecular weight from the $^{31}$P NMR spectrum.

The chain length of the novel polyphosphinic acids and their salts can be simply controlled and widely varied via the choice of reaction conditions. The most important control element here is the ratio of the starting materials. If, for example, equimolar amounts of hypophosphite and acetylene are used and the reaction time and temperature are high, particularly high-molecular-weight polyphosphinic acids are produced, where ū>100. If the molar ratio of starting materials used is, for example, 1 (hypophosphite) to 0.75 (acetylene), a particularly low-molecular-weight polyphosphinic acid is produced, where the average chain length ū3.

In the case of gaseous acetylenes, such as the parent compound acetylene itself, the reaction can be controlled via the duration of gas feed. The longer the acetylene feed continues, the longer the chains which are built up.

What has been said above applies in particular to compounds which are produced by reaction scheme A described above.

Polymeric phosphinic acids and their salts which preferably have vinyl end groups are obtained in particular by the process described in reaction scheme B.

In this case:

If the rate of the addition reaction to the vinylphosphonous acid (reaction 2) is markedly slower than the addition reaction to the acetylene (reaction 1), the following reaction scheme is likely for polyaddition leading to polyphosphinic acid type B:

Reaction scheme B:

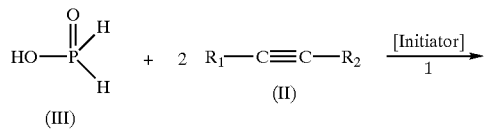
(III)
Hypophosphorous acid

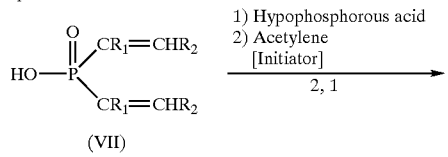
(VII)
Divinyl phosphinic acid

-continued
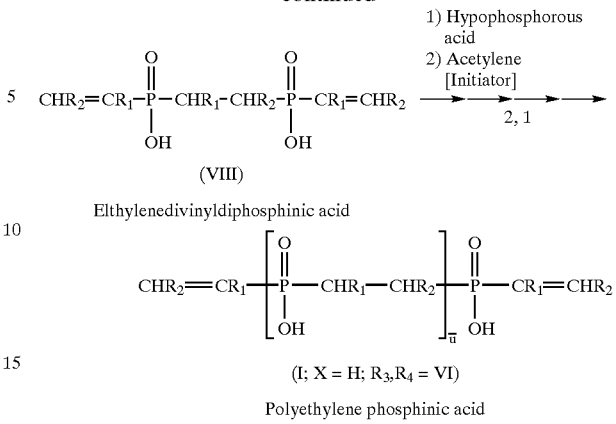
(VIII)
Elthylenedivinyldiphosphinic acid $$CHR_2=CR_1-\left[\begin{array}{c}O\\\parallel\\P\\\mid\\OH\end{array}-CHR_1-CHR_2\right]_{\bar{u}}\begin{array}{c}O\\\parallel\\P\\\mid\\OH\end{array}-CR_1=CHR_2$$

(I; X = H; $R_3,R_4$ = VI)

Polyethylene phosphinic acid

This reaction pathway, which leads to polyphosphinic acids with vinyl end groups (type B), is found especially when acetylenes having bulky groups are used.

The reaction here may be followed, and also the chain length determined, using combined $^{31}$P and $^1$H NMR spectroscopy. The ratio of the end groups to the nonterminal chain units, and thus the average chain length in (I), can be determined here via the ratio of the absorptions of the terminal vinyl protons to the absorptions of the ethylene-bridge protons.

In the polyaddition which follows this scheme, the chain length of the novel polyphosphinic acids can again be readily controlled and widely varied via the choice of reaction conditions and especially via the ratio of the starting materials.

If, for example, equimolar amounts of hypophosphite and acetylene are used and the reaction time and reaction temperature are high, particularly high-molecular-weight polyphosphinic acids are produced, where ū>100.

If, for example, the molar ratio of starting materials used is 1 (hypophosphite) to 1.25 (acetylene), low-molecular-weight polyphosphinic acid is produced, where ū=3.

As will be clear from what has been stated above, the compounds described above of the formulae (IV), (V), (VII) and (VIII) are also provided by the present invention. With appropriate optimization of the process they can be isolated and identified at a suitable point.

The two fundamental reaction pathways A and B indicated here may also proceed in parallel to one another and give polyphosphinic acids with a mixture phosphonous acid end groups and vinyl end groups, as also defined more precisely in claims 13 and 14, for example.

According to the present invention, two hypophosphite radicals are involved in a stepwise addition reaction with the triple bond, as described in the two possible reaction schemes (A and B) and in formula (I), preferably 1,2 addition.

Depending on the steric and electronic influences exerted by the substituents ($R_1$ and $R_2$) in the acetylene used, 1,1-addition is also possible, i.e. structural units of the following type may also be present in the polymeric phosphinic acids:

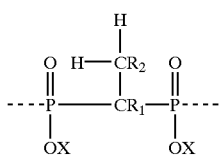

The present invention also provides polymeric phosphinic acids and their salts which contain these structural units.

In addition, especially if the reaction is carried out in dilute solution, cyclopolyaddition may also produce byproducts which are cyclopolyphosphinic acids and, respectively, their salts of the formula (IX)

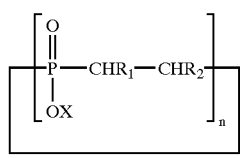

(IX)

where X is a hydrogen atom or a 1/m metal of valency m, $R_1$ and $R_2$ may be identical or different and are hydrogen, a carboxyl group, a carboxylic acid derivative, an unsubstituted or substituted alkyl group having 1 to 10 carbon atoms, phenyl, benzyl or alkyl-substituted aromatics, and in which n is a number from 2 to 100.

Such cyclopolyphosphinic acids and, respectively, their salts of the formula (IX) are also provided by the present invention.

Variation of the novel polymeric phosphinic acids and of their properties may be achieved not only in terms of their prevailing end group but also by numerous possibilities for the choice of reaction conditions and especially the choice of reactants.

EXAMPLES

Example 1

Polyethylenephosphinic Acid

Over a period of 30 h at a temperature of about 100° C., gaseous acetylene was introduced into a solution of 106 g of sodium hypophosphite (1 mol) in 250 ml of glacial acetic acid in a heatable tubular glass reactor with a frit for gas introduction. A solution of 27 g (10 mol%) of 2,2'-azobis (2-amidinopropane) dihydrochloride in 500 g of a water/acetic acid mixture (1:3) was fed at a uniform rate over this entire period. After a time of 0.5 h for continued reaction, removal of the acetylene by flushing with nitrogen, and cooling to room temperature, the reaction mixture was freed from solvent, taken up in 400 ml of water and mixed with 100 ml of concentrated hydrochloric acid. The resultant precipitate was filtered, washed with 2×200 ml of water and dried at 130° C. under the suction provided by a water jet. This gave 82 g of a white powder, corresponding to a yield of 77.4%, based on hypophosphite used. Elemental analysis confirms the structure proposed for the polymer: P: calc. 33.7%—found 31.6%; C: calc. 26.1%—found 26.7%; H: calc. 5.4%—found 5.7%. The following signals were found in the $^{31}$P NMR spectrum (NaOD):

δ=45–53 ppm: broad multiplets (polymeric phosphinic acid groups): integral: 95 δ=30–35 ppm: broad multiplet (phosphonous acid end groups): integral: 1.3 calculated average chain length: $\bar{u}=147$

Example 2

Polyethylenephosphinic Acid

Over a period of 9 h at a temperature of about 100° C., gaseous acetylene was introduced into a solution of 106 g of sodium hypophosphite (1 mol) in 250 ml of glacial acetic acid in a heatable tubular glass reactor with a frit for gas introduction. A solution of 8.1 g (3 mol%) of 2,2'-azobis(2-amidinopropane) dihydrochloride in 150 g of a water/acetic acid mixture (1:3) was fed at a uniform rate over this entire period. After a time of 0.5 h for continued reaction, removal of the acetylene by flushing with nitrogen, and cooling to room temperature, the reaction mixture was freed from solvent, taken up in 400 ml of water and mixed with 100 ml of concentrated hydrochloric acid. The resultant precipitate was filtered, washed with 2×200 ml of water and dried at 130° C. under the suction provided by a water jet. This gave 79 g of a white powder, corresponding to a yield of 74.5%, based on hypophosphite used. Elemental analysis confirms the structure proposed for the polymer: P: calc. 33.7%—found 31.6%;, C: calc. 26.1%—found 25.0%; H: calc. 5.4%—found 5.6%. The following signals were found in the $^{31}$P NMR spectrum (NaOD):

δ=45–53 ppm: broad multiplets (polymeric phosphinic acid groups): integral: 87 δ=30–35 ppm: broad multiplet (phosphonous acid end groups): integral: 12.6 calculated average chain length: $\bar{u}=15$

Example 3

Polyethylenephosphinic Acid

Over a period of 6 h at a temperature of about 100° C., gaseous acetylene was introduced into a solution of 106 g of sodium hypophosphite (1 mol) in 250 ml of glacial acetic acid in a heatable tubular glass reactor with a frit for gas introduction. A solution of 5.4 g (2 mol%) of 2,2'-azobis(2-amidinopropane) dihydrochloride in 150 g of a water/acetic acid mixture (1:3) was fed at a uniform rate over his entire period. After a time of 0.5 h for continued reaction, removal of the acetylene by flushing with nitrogen, and cooling to room temperature, the reaction mixture was freed from solvent, taken up in 400 ml of water and mixed with 100 ml of concentrated hydrochloric acid. The resultant precipitate was filtered, washed with 2×200 ml of water and dried at 130° C. under the suction provided by a water jet. This gave 70 g of a white powder, corresponding to a yield of 66.0%, based on hypophosphite used. Elemental analysis confirms the structure proposed for the polymer: P: calc. 33.7%—found 32.5%; C: calc. 26.1%—found 25.7%; H: calc. 5.4%—found 5.5%. The following signals were found in the $^{31}$P NMR spectrum (NaOD):

δ=45–53 ppm: broad multiplets (polymeric phosphinic acid groups): integral: 49 δ=30–35 ppm: broad multiplet (phosphonous acid end groups): integral: 42 calculated average chain length: $\bar{u}=3.3$

Example 4

Sodium Salt of Polyethylenephosphinic Acid 41 g (0.45 mol) of the polyethylenephosphinic acid obtained in Example 1 were slowly introduced into a solution of 18 g (0.45 mol) of NaOH in 100 ml of water, giving a clear solution. Removal of the water and drying at 130° C. under the suction provided by a water jet gave 50.8 g of the sodium salt of polyethylenephosphinic acid, corresponding to a yield of 100%.

Example 5

Aluminum Salt of Polyethylenephosphinic Acid 41 g (0.45 mol) of the polyethylenephosphinic acid obtained in Example 1 were slowly introduced into a solution of 18 g (0.45 mol) of NaOH in 100 ml of water, giving a clear solution of the sodium salt of the polyethylenephosphinic acid. A solution of 50 g (0.075 mol) of $Al_2(SO_4)_3 \cdot 18H_2O$ in 50 ml of water was then added dropwise. The salt which precipitates immediately was filtered off and washed with 2×100 ml of water. Drying at 130° C. under the suction provided by a water jet gave 43.8 g of the aluminum salt of polyethylenephosphinic acid, corresponding to a yield of 96%.

Example 6

Aluminum Salt of Polyethylenephosphinic Acid

Over a period of 30 h at a temperature of about 100° C., gaseous acetylene was introduced into a solution of 106 g of sodium hypophosphite (1 mol) in 250 ml of glacial acetic acid in a heatable tubular glass reactor with a frit for gas introduction. A solution of 27 g (10 mol%) of 2,2'-azobis(2-amidinopropane) dihydrochloride in 500 g of a water/acetic acid mixture (1:3) was fed at a uniform rate over this entire period. After a time of 0.5 h for continued, reaction, 24 g (0.3 mol) of aluminum hydroxide were added and the reaction mixture was heated to 80° C. for 4 h and then at reflux (112° C.) for 5 h. This was followed by filtration, washing with 2×200 ml of water and drying at 130° C. under the suction provided by a water jet. This gave 72 g of the aluminum salt of polyethylenephosphinic acid, corresponding to a yield of 72%, based-on hypophosphite used.

The following signals were found in the $^{31}P$ NMR spectrum (NaOD):

δ=45–53 ppm: broad multiplets (polymeric phosphinic acid groups): integral: 88 δ=30–35 ppm: broad multiplet (phosphonous acid end groups): integral: 0.3 calculated average chain length: $\bar{u}$=588.

The novel phosphinic acids represent an entirely new class of polymers, the properties of which can be varied very widely.

What is claimed is:

1. A polymeric phosphinic acid or a salt thereof of the formula (I)

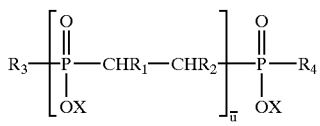

in which

X is hydrogen cerium or a metal selected from the group consisting of a metal of group IA, IIA, IIIA, IVA, VA, IIB, IVB, VIIB, and VIIIB of the Periodic Table, $R_1$ and $R_2$ are identical or different and are hydrogen, a carboxyl group, a carboxylic acid ester or nitrile group, an unsubstituted or substituted alkyl group having 1 to 10 carbon atoms, phenyl, benzyl or alkyl-substituted aromatics, $R_3$ and $R_4$ are identical or different and are hydrogen or a vinyl group of the formula (VI)

$$—CR_1\!\!=\!\!CHR_2 \quad (VI)$$

in which $R_1$ and $R_2$ have the abovementioned meaning, and $\bar{u}$ is the average number of monomer units, and is at least 1.

2. A polymeric phosphinic acid or a salt thereof as claimed in claim 1, wherein the metal is Li, Na, K, Mg, Ca, Sr, Ba, Al, Ge, Sn, Sb, Bi, Zn, Ti, Zr, Mn, Fe and/or Ce.

3. A polymeric phosphinic acid or a salt thereof as claimed in claim 1, wherein the metal is Na, Ca, Al and/or Zn.

4. A polymeric phosphinic acid or a salt thereof as claimed in claim 1, wherein X is H.

5. A polymeric phosphinic acid or a salt thereof as claimed in claim 1, wherein $R_1$ and $R_2$ are identical or different and are hydrogen or an unsubstituted or substituted alkyl group having 1 to 10 carbon atoms.

6. A polymeric phosphinic acid or a salt thereof as claimed in claim 1, wherein $R_1$ and $R_2$ are identical or different and are hydrogen or an unsubstituted or substituted alkyl group having 1 to 10 carbon atoms, where the substituents are one or more of the groups OH, CN or $NH_2$.

7. A polymeric phosphinic acid or a salt thereof as claimed in claim 1, wherein $R_1$ and $R_2$ are identical or different and are hydrogen or an alkyl group having from 1 to 4 carbon atoms and substitution by one or two OH groups.

8. A polymeric phosphinic acid or a salt thereof as claimed in claim 1, wherein $R_1$ and $R_2$ are identical or different and are hydrogen or a carboxylic acid derivative.

9. A polymeric phosphinic acid or a salt thereof as claimed in claim 8, wherein $R_1$ and $R_2$ are identical or different and are hydrogen or a carboxylic acid derivative of the formula COOR and R is an alkyl group having from 1 to 4 carbon atoms.

10. A polymeric phosphinic acid or a salt thereof as claimed in claim 1, wherein $R_3$ and $R_4$ are hydrogen.

11. A polymeric phosphinic acid or a salt thereof as claimed in claim 1, wherein each of $R_3$ and $R_4$ is a vinyl group of the formula —$CR_1$=$CHR_2$ (VI), in which $R_1$ and $R_2$ have the abovementioned meanings.

12. A polymeric phosphinic acid or a salt thereof as claimed in claim 1, wherein $R_3$ is H and $R_4$ is a vinyl group of the formula —$CR_1$=$CHR_2$ (VI), in which $R_1$ and $R_2$ have the abovementioned meanings.

13. A polymeric phosphinic acid or a salt thereof as claimed in claim 1, wherein $R_3$ is a vinyl group of the formula —$CR_1$=$CHR_2$ (VI), in which $R_1$ and $R_2$ have the abovementioned meanings and $R_4$ is H.

14. A polymeric phosphinic acid or a salt thereof as claimed in claim 11, wherein each of $R_1$ and $R_2$ is an identical or different alkyl group having 1 to 10 carbon atoms or is hydrogen.

15. A polymeric phosphinic acid or a salt thereof of the formula

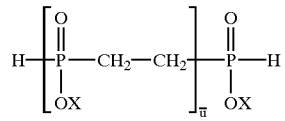

where X=H, cerium or a metal selected from the group consisting of a metal of group IA, IIA, IIIA, IVA, VA, IIB, IVB, VIIB, and VIIIB of the Periodic Table, and where $\bar{u}$ is at least 1.

16. A polymeric phosphinic acid or a salt thereof of the formula

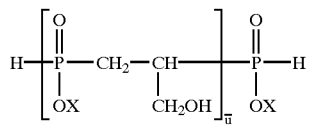

where X=H, cerium or a metal selected from the group consisting of a metal of group IA, IIA, IIIA, IVA, VA, IIB, IVB, VIIB, and VIIIB of the Periodic Table, and where ū is at least 1.

17. A polymeric phosphinic acid or a salt thereof of the formula

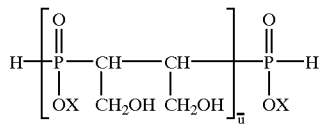

where X=H, cerium or a metal selected from the group consisting of a metal of group IA, IIA, IIIA, IVA, VA, IIB, IVB, VIIB, and VIIIB of the Periodic Table, and where ū is at least 1.

18. A polymeric phosphinic acid or a salt thereof of the formula

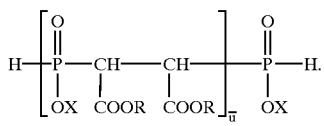

where X=H, cerium or a metal selected from the group consisting of a metal of group IA, IIA, IIIA, IVA, VA, IIB, IVB, VIIB, and VIIIB of the Periodic Table, and ū is at least 1, and where R is an alkyl group having from 1 to 4 carbon atoms.

19. A flame retardant comprising the polymeric phosphinic acids and/or their salts as claimed in claim 1.

20. A method for producing a flame retardant thermoplastic polymer comprising the step of adding the polymeric phosphinic acids and/or their salts as claimed in claim 1 to a thermoplastic polymer.

21. A method for preparing synthetic building blocks for synthesis in organophosphorus chemistry, comprising the step of adding the polymeric phosphinic acids and/or their salts as claimed in claim 1 to a organophosphorus compound.

* * * * *